United States Patent [19]

Shook, Jr.

[11] 4,347,193

[45] Aug. 31, 1982

[54] ARYL BORANE COMPLEXES

[75] Inventor: Howard E. Shook, Jr., Orange, Tex.

[73] Assignee: E. I. Du Pont de Nemours and Company, Wilmington, Del.

[21] Appl. No.: 31,978

[22] Filed: Apr. 20, 1979

[51] Int. Cl.$^2$ ............................................. C07F 15/04
[52] U.S. Cl. ............................ 260/439 R; 252/431 N
[58] Field of Search ..................................... 260/439 R

[56] References Cited

U.S. PATENT DOCUMENTS 3,372,006  3/1968  Chamberland et al. ... 260/606.5 B X
4,046,815  9/1977  Nazarenko ................... 260/606.5 B
4,076,756  2/1978  Nazarenko et al. .......... 260/606.5 B
4,082,811  4/1978  Shook .......................... 260/606.5 B
4,134,923  1/1979  Reimer ......................... 260/606.5 B Primary Examiner—Helen M. S. Sneed

[57] ABSTRACT

A novel compound having the general formula $Ni[NH_3]_4[(NC)B(C_6H_4-R)_3]_2$ wherein R is selected from the group consisting of hydrogen, halogen, alkyl groups having 1–6 carbon atoms and aryl groups having 6–10 carbon atoms prepared by reacting a nickel compound with the cyanide adduct of a triarylborane. The novel compounds can be converted to a cyanide free adduct of the triarylborane.

4 Claims, No Drawings

ARYL BORANE COMPLEXES

BACKGROUND OF THE INVENTION

1. Field of the Invention

The present invention relates to novel complexes of triarylboranes and, more particularly, to a nickel cyanide triphenylborane complex. The complex may be reacted to produce an adduct of triphenylborane which may be subsequently converted to the free borone which is used as a catalyst promoter in the hydrocyanation of butadiene.

2. Description of the Prior Art

The preparation of a compound postulated to be the sodium cyanide adduct of triphenylborane having a formula [$\phi_3$(CN)B]Na was reported by G. Wittig et al [Ann. Chem., 573, 195 (1951)]. This article also disclosed the production of triphenylborane by thermally decomposing a mixture of compounds of the formula $(CH_3)_3NH^+B(C_6H_5)_4^-$ as well as the preparation of the sodium hydroxide salt of triphenylborane by fusing of the borane with sodium hydroxide and the reaction of that salt with ammonium chloride or hydroxide to yield the ammonia adduct of triphenylborane. This adduct was reacted with dry hydrochloric acid in the presence of ether by Mikhailov et al. [Izvest. Akad Nauk S.S.S.R., Otdel. Kimm. Nauk, 812 (1957)] to produce triphenylborane and ammonium chloride. Production of complex salts of boranes, for example, the reaction of $(C_6H_5)_3BNH_3$ with quarternary ammonium fluoride and hydroxide salts in the presence of ethanol to produce complex salts is disclosed by D. L. Fowler and C. A. Krauss, J. Am. Chem. Soc. 62, 1143 (1940).

SUMMARY OF THE INVENTION

A novel compound having the general formula $Ni[NH_3]_4[(NC)B(C_6-R)_3]_2$ wherein R is selected from the group consisting of hydrogen, halogen, alkyl groups having 1–6 carbon atoms and aryl groups having 6–10 carbon atoms is prepared by reacting a nickel compound with the cyanide adduct of a triarylborane. The novel compound can be converted to a cyanide free adduct of the triarylborane.

DETAILED DESCRIPTION OF THE INVENTION

The nickel halides which can be employed to prepare the composition of the present invention include $NiCl_2$, $NiBr_2$, $NiI_2$ and their hydrates such as $NiCl_2.6H_2O$, $NiBr_2.6H_2O$, and $NiI_2.XH_2O$ and their ammine complexes such as $[Ni(NH_3)_6]Cl_2$, $[Ni(NH_3)_6]Br_2$, and $[Ni(NH_3)_6]I_2$.

The alkali metal cyanide adduct of the triarylboranes which can be employed to prepare the composition of the present invention include the sodium cyanide adducts of triphenylborane, tri-o-tolylborane, tri-p-tolylborane, tri-p-chloro phenylborane, tri-p-bromophenylborane, tri-diphenylborane, tri-naphthylphenylborane and tri-n-hexylphenylborane.

The reactants are preferably dissolved in a suitable reaction medium (solvent) prior to contact. Such media include water, methanol, ethanol, and acetonitrile and others which are essentially inert with respect to the reactants and products. Water is the preferred medium.

The reaction is conducted at a temperature in the range of 5° to 70° C. and preferably in the range 20° to 30° C. to provide an acceptable rate of reaction while avoiding decomposition of the complex.

The following examples are presented to illustrate but not to restrict the present invention. Parts and percentages are by weight unless otherwise noted.

EXAMPLE 1

A solution was prepared by dissolving 0.7518 g of nickel chloride hexahydrate $[NiCl_2(H_2O)_6]$ and 50 ml of concentrated ammonium hydroxide (28–30% $NH_3$) at room temperature. Another solution was prepared by dissolving 1.7996 g of the sodium cyanide adduct of triphenylborane [$Na(C_6H_5)_3BCN$] in 20 ml of water at room temperature. The solution of cyanide adduct was then added slowly to the nickel chloride solution with stirring while maintaining the reactants at ambient pressure and at a temperature of about 25° C. During the addition a purple solid precipitated from the reaction medium. This solid was recovered by vacuum filtration at room temperature, then washed with 100 ml of concentrated ammonium hydroxide following which the washed filter cake was dried under vacuum at 50° C. for 4 hours. The resulting dry, pale purple solid which weighed 1.7716 g was submitted for infra-red and elemental analysis. The infra-red spectrum showed a band at 2190 cm$^{-1}$ (CN) and a band at 1225 cm$^{-1}$ ($NH_3$). The elemental analysis and the analysis for the equivalent of triphenylborane as well as the calculated composition of the complex $Ni[NH_3]_4[(NC)B(C_6H_5)_3]_2$ are set forth below:

| Composition (%) by | C | H | N | Ni | B | $(C_6H_5)_3B$ |
|---|---|---|---|---|---|---|
| Analysis | 67.17 | 6.70 | 14.58 | 8.04 | 3.44 | 72.8 |
| Calculation | 68.83 | 6.38 | 12.67 | 8.85 | 3.76 | 73.0 |

A comparison of the analytical and calculated data indicates that the composition of the complex is as set forth above.

EXAMPLE 2

The sodium cyanide adduct of tri-p-chlorophenylborane [$Na(p-ClC_6H_4)_3BCN$] was prepared by combining 2.184 g of the ammonia adduct of tri-p-chlorophenylborane [$(p-ClC_6H_4)_3B.NH_3$] and 0.29 g of sodium cyanide in 100 ml of distilled water following which the solution was distilled at atmospheric pressure until 80 ml of ammonium hydroxide were recovered overhead. Approximately 100 ml of water were then added to the residue in the distillation flask and an additional 100 ml of dilute ammonium hydroxide were removed by distillation at atmospheric pressure. This resultant solution was then added slowly with stirring at room temperature to a solution prepared by dissolving nickel chloride hexahydrate (0.7104 g) in 50 ml of concentrated ammonium hydroxide (28–30% $NH_3$). A pale blue precipitate which formed as the two solutions were combined was collected by vacuum filtration, washed with approximately 100 ml of concentrated ammonium hydroxide and then dried under vacuum at 50° C. for 4 hours. The resultant product which weighed 2.3932 g was submitted for infra-red and elemental analysis. The infra-red spectrum showed a band at 2190 cm$^{-1}$ (CN) and a band at 1225 cm$^{-1}$ ($NH_3$). The elemental analysis as well as the calculated composition are set forth below:

| Composition (%) by | C | H | N | B | Ni | CL |
|---|---|---|---|---|---|---|
| Analysis | 52.77 | 4.10 | 8.43 | 2.33 | 5.74 | 24.73 |
| Calculation | 52.47 | 4.17 | 9.66 | 2.49 | 6.75 | 24.46 |

The results show that a complex of the formula $Ni[NH_3]_4[(CN)B(C_6H_4Cl\text{-}p)_3]_2$ was prepared.

EXAMPLE 3

The sodium cyanide adduct of tri-p-tolylborane was prepared by dissolving 3.0071 g of the ammonia adduct of tri-p-tolylborane $[(p\text{-}CH_3C_6H_4)_3B\cdot NH_3]$ and 0.4906 g of sodium cyanide in 100 ml of distilled water following which the solution was distilled at atmospheric pressure to remove approximately 75 ml of ammonium hydroxide. An additional 100 ml of distilled water were then added to the residue in the distillation flask and approximately 105 ml of dilute ammonium hydroxide were then removed by distillation. The resultant solution was added to a solution of nickel chloride hexahydrate prepared by dissolving 1.1902 g of the hydrate in 50 ml of concentrated ammonium hydroxide (28–30% $NH_3$) with agitation at room temperature. The pale blue precipitate which formed during the combination of the two solutions was collected by vacuum filtration, washed with 100 ml of concentrated ammonium hydroxide and dried under vacuum at 50° C. for 16 hours. This product which weighed 3.2141 g was submitted for elemental analysis. The results of the analysis and the calculated formula for the complex $Ni[NH_3]_4[(NC)B(C_6H_4CH_3\text{-}p)_3]_2$ are set forth below.

| Composition (%) by | C | H | N | B | Ni |
|---|---|---|---|---|---|
| Analysis | 71.59 | 7.40 | 10.80 | 2.77 | 7.40 |
| Calculation | 70.72 | 7.28 | 11.25 | 2.90 | 7.86 |

The results show that the nickel-boron complex having the above formula was prepared.

EXAMPLE 4

A sodium cyanide adduct of tri-o-tolylborane was prepared by dissolving 2.1731 g of the tri-o-tolylborane ammonia adduct $[(o\text{-}CH_3C_6H_4)_3BNH_3]$ and 0.3495 g of sodium cyanide in 100 ml of distilled water, following which approximately 80 ml of ammonium hydroxide was distilled from the solution at atmospheric pressure. An additional 100 ml of distilled water was then added to the distillation flask and 100 ml of dilute ammonium hydroxide distilled therefrom. This resultant solution was then combined at room temperature under agitation with a solution prepared by dissolving 0.8608 g of nickel chloride hexahydrate in 50 ml of concentrated ammonium hydroxide (28–30% $NH_3$). The gray precipitate which formed as the solutions were combined was collected by vacuum filtration, washed with 100 ml of concentrated ammonium hydroxide and then dried under vacuum at 50° C. for 4 hours. The product which weighed 2.4069 g was submitted for elemental analysis. The results of the analysis and the calculated formula for the complex $Ni[NH_3]_4[(NC)B(C_6H_4CH_3\text{-}o)_3]_2$ are set forth below.

| Composition (%) by | C | H | N | B | Ni |
|---|---|---|---|---|---|
| Analysis | 69.16 | 7.53 | 12.34 | 2.99 | 7.52 |
| Calculation | 70.72 | 7.28 | 11.25 | 2.90 | 7.86 |

The complexes of the present invention may be converted to the ammonia adduct of the respective borane by heating the complex in an aqueous medium containing sodium hydroxide or ammonium hydroxide at elevated temperatures, e.g., 100° C. Nickel can be precipitated as a nickel hydroxide which can be separated from the solution when sodium hydroxide is used. Following precipitation of the nickel hydroxide, ammonia can be added to precipitate the ammonia adduct of the triarylborane. Nickel remains in solution when ammonium hydroxide is used and the ammonia adduct of the triarylborane precipitates. Subsequently, the ammonia adduct of the triarylborane can be converted to the free borane by known methods.

I claim:

1. A compound having the general formula $Ni[NH_3]_4[(NC)B(C_6H_4\text{-}R)_3]_2$ wherein R is selected from the group consisting of hydrogen, halogen, alkyl groups having 1–6 carbon atoms and aryl groups having 6–10 carbon atoms.
2. The compound of claim 1 wherein R is hydrogen.
3. The compound of claim 1 wherein R is methyl.
4. The compound of claim 1 wherein R is chlorine.

* * * * *